United States Patent [19]

Thompson

[11] Patent Number: 4,627,095
[45] Date of Patent: Dec. 2, 1986

[54] ARTIFICIAL VOICE APPARATUS

[76] Inventor: Larry Thompson, 3505 W. Rochelle Rd., Irving, Tex. 75062

[21] Appl. No.: 600,127

[22] Filed: Apr. 13, 1984

[51] Int. Cl.⁴ .............................................. A61F 1/20
[52] U.S. Cl. ............................................................ 381/70
[58] Field of Search ................... 340/404, 405; 381/70, 381/86, 71; 623/9

[56] References Cited

U.S. PATENT DOCUMENTS

| | | | |
|---|---|---|---|
| 1,156,329 | 10/1915 | Thomas | 84/330 |
| 1,633,705 | 6/1927 | McKesson . | |
| 1,685,824 | 10/1928 | McKesson . | |
| 1,835,757 | 12/1931 | Burchett . | |
| 1,836,816 | 12/1931 | Riesz . | |
| 1,840,112 | 1/1932 | Lane . | |
| 1,867,350 | 7/1932 | Burchett . | |
| 1,901,433 | 3/1933 | Burchett . | |
| 1,910,966 | 5/1933 | Riesz . | |
| 1,922,385 | 8/1933 | McKesson | 3/1 |
| 1,985,013 | 12/1934 | Burchett | 623/9 |
| 2,024,601 | 12/1935 | Riesz | 3/1 |
| 2,041,487 | 1/1934 | Riesz | 3/1 |
| 2,056,295 | 10/1936 | Riesz | 3/1 |
| 2,058,212 | 10/1936 | Burchett | 3/1 |
| 2,273,077 | 2/1942 | Wright | 272/14 |
| 2,479,738 | 8/1949 | Goldstein et al. | 84/330 |
| 2,862,209 | 12/1958 | Cooper | 3/1.3 |
| 3,066,186 | 11/1962 | Trammell | 179/1 |
| 3,084,221 | 4/1963 | Cooper et al. | 179/1 |
| 3,291,912 | 12/1966 | Flanagan | 179/1 |
| 3,766,318 | 10/1973 | Webb | 179/1 |
| 3,914,550 | 10/1975 | Cardwell | 179/1 |
| 4,060,856 | 12/1977 | Edwards | 3/1.3 |
| 4,223,411 | 9/1980 | Schoendorfer et al. | 3/1.3 |
| 4,264,989 | 5/1981 | Wiley | 3/1.3 |
| 4,280,492 | 7/1981 | Latham | 128/207.15 |
| 4,292,472 | 9/1981 | Lennox | 179/1 |
| 4,338,488 | 7/1982 | Lennox | 179/1 |
| 4,489,440 | 12/1984 | Chaoui | 381/70 |

Primary Examiner—Forester W. Isen
Attorney, Agent, or Firm—Hubbard, Thurman, Turner & Tucker

[57] ABSTRACT

An artificial voice apparatus including a pump for producing an airflow within a tube. The tube is connected to a sounding mechanism for combining an audible sound with the airflow. A mouthpiece including a second tube is connected to the sounding mechanism to transport the combined sound and airflow to within a person's mouth. The combination of airflow and sound within the person's mouth enables the person to use the tongue, lips and teeth to articulate the sound to form speech.

12 Claims, 11 Drawing Figures

ARTIFICIAL VOICE APPARATUS

BACKGROUND

1. Field of the Invention

This invention relates to the production of sound and air within a person's mouth to enable that person to speak and more particularly to a mechanism that combines an audible sound with an airflow while transporting this combination to the person's mouth to be articulated as speech.

2. Description of the Prior Art

Many persons are deprived of speech because of the inability of their larynx to produce sound and, in some cases, the inability to exhale through the mouth. Specifically, a person with a respirator tube positioned in the mouth and down the throat cannot speak since the tube is controlling their breathing and also blocking the larynx.

In the prior art, a tracheostomy tube was disclosed in U.S. Pat. No. 4,280,492 to Latham that permits a person with a tracheostomy, a respirator tube entering at the base of the throat, to speak by providing dual airflow. The first flow of air is provided to the lungs for breathing and a second flow of air is provided to the upper throat through the larynx to allow speech. However, in a situation where the patient does not have a tracheostomy but rather has the respirator tube entering into the mouth and going down the throat, the larynx is still blocked preventing speech.

Several attempts have been made at producing audible sound within a person's mouth from a sound source external to the person's mouth. U.S. Pat. No. 2,041,487 entitled "Artificial Larynx" to Riesz provides a diaphragm mechanism that produces a sound that is transmitted through a tube into a person's mouth allowing the person to speak. U.S. Pat. No. 4,292,472 entitled "Electronic Artificial Larynx" to Lennox also contains a tone generator connected to a pair of eye galsses worn by the patient. The tone generator is connected to a tube that transmits the sound to the person's mouth for speech. U.S. Pat. No. 3,084,221 entitled "Speech Aid" to Cooper et al also provides a sound generator connected to a tube which is connected to a mechanism held by the patient's teeth that enables sound waves to be transmitted inside the patient's mouth for speech. U.S. Pat. No. 2,273,077 entitled "Means and Method of Producing Sound Effects" to Wright illustrates an external sound generating source connected to a tube with the tube inserted into a person's nose to transmit sound into the mouth cavity. All of these perior art patents produce sound for articulation by the patient. However, the sound produced requires breathing for proper articulation. In instances, where the sound is produced with little breathing, the articulation of the sound becomes difficult.

It is the object of the present invention to produce sound capable of articulation without requiring the patient to breath.

SUMMARY OF THE INVENTION

In accordance with the present invention an artificial voice apparatus is disclosed that includes a mechanism for producing an airflow within an airflow transmission device. The airflow transmission device is connected to a combining mechanism that combines the airflow with an audible sound. A mouthpiece deposits the combined sound and air within a person's mouth in such a way to allow the person to articulate the sound to produce speech.

In a preferred embodiment, the combining mechanism includes a modulator to modulate the airflow to produce the combination of airflow with audible sound. The sound is produced at a selected frequency that may be controlled by the user. In this preferred embodiment, the modulator includes a rotating disk with a plurality of slots. The disk is located in the path of the airflow and the rotation of the disk intermittently interrupts the airflow to generate the sound at the selected frequency. The frequency of sound can be controlled by the number of slots in the disk, by the speed of rotation of the disk, by the thickness of the disk or by the shapes of the slots. Additionally, the slots may be placed on the disk in various patterns to produce sound with various overtones.

In another preferred embodiment, the combining mechanism includes an enclosure connected to receive the airflow. The enclosure includes one or more speakers that are electrically connected to a signal generator for producing sound. The enclosure is also connected to the mouthpiece mechanism and combines the sound with the airflow by generating the sound from the speaker in the presence of the airflow.

In a still further embodiment, an artificial voice apparatus is disclosed that includes an enclosure with the speaker mounted to divide the enclosure into a first chamber and a second chamber with the forward portion of the speaker facing the first chamber and the rearward portion of the speaker facing the second chamber. The first and second chambers are each connected to an individual input valve that provides for air to be placed in the respective chamber when the pressure inside the chamber is less than the atmospheric pressure outside the chamber but prevents air from leaving the respective chambers through the valve when the pressure in the respective chamber is greater than the pressure outside the enclosure. The speaker is electrically connected to a signal generator having the speaker produce an audible sound and also producing an airflow by having the speaker paper vibrate as a diaphragm to produce an airflow in combination with the valves of the chambers. The mouthpiece mechanism is connected on the oppsite side of the enclosure from the input valves and includes two output valves provided to allow airflow from the chambers without allowing air to return to the chambers. A structure connected to the output valves combines the two airflows from the two chambers together with the sounds produced and transports this combination to the person's mouth for articulation and speech.

In an additional embodiment, a combining mechanism is disclosed which includes a first enclosure structured to receive the airflow on one side. The opposing side includes several holes. A second similar, but mirror-imaged to the first, enclosure is placed in proximity with the first, the holes of the second being aligned with the holes of the first providing a path for the airflow. Located between these enclosures is a plate which also includes several holes. The plate is connected to an oscillating device such as a solenoid which causes the plate to move in a manner to intermittently interrupt the flow of air between the two enclosures resulting in a sound being generated and combined with the airflow. A similar embodiment includes a first enclosure with a cylindrical portion containing several holes on the cylinder surface. A second enclosure including a cylindrical cavity is provided. This second enclosure cavity includes several holes in the cylinder surface. The first cylinder is mounted with its cylindrical portion within the cylindrical cavity of the second enclosure. Either enclosure is set into oscillatory motion relative to the other enclosure by connection to an oscillating source such as a solenoid. One enclosure is structured to receive the airflow and the other enclosure is structured to output the airflow. The oscillatory action results in an intermittent interruption of the airflow generating a sound that is combined with the airflow. In either of the above two embodiments, both enclosures may be set in an oscillatory motion, but with opposite phase, to double the effective motion.

In a still further embodiment, an artificial voice apparatus is disclosed that includes a pump for producing an airflow within a first tube. This tube is connected to a control device for selectively directing the airflow from the first tube to a second tube or to the outside atmosphere. A sounding mechanism is connected to the second tube and receives this airflow and combines the airflow with an audible sound. A mouthpiece mechanism is connected to the sounding mechanism for transporting the combined sound and airflow to a location within a person's mouth in order that this sound and airflow may be articulated as speech. In this preferred embodiment, the sound and airflow are deposited in the person's mouth behind the person's tongue and below the roof of the mouth.

A further embodiment is disclosed that includes a mouthpiece with a reed-type sounding device at its furtherest end. As airflow is forced through the mouthpiece, sound is created by the sounding device. The person then articulates the combined airflow and sound as speech.

In a similar embodiment, and electronic sounding device such as a piezo electric transducer is placed at the end of the mouthpiece in the persons' mouth. The sounding device is connected to an electronic circuit which causes sound to be emitted from the sounding device. As airflow is passed through the mouthpiece, the sound is combined with the airflow. The person then articulates this combined airflow and sound as speech.

In a still further embodiment of this invention, a speaker apparatus is disclosed that includes a mechanism for producing two airflows. An enclosure is connected to receive the airflows and includes a speaker mounted to divide the enclosure into a first chamber and a second chamber. The first chamber has the forward portion of the speaker facing it and the second chamber has the rearward portion of the speaker facing it. The first chamber receives one airflow and the second chamber receives the second airflow. The speaker is electrically connected to a signal source to receive electrical signals for conversion into audible sound which is combined with the airflows in the respective chambers. The enclosure is also structured to combine the output airflows from these chambers and to emit the airflows with the sound.

BRIEF DESCRIPTION OF THE DRAWINGS

The above and other features and advantages of this invention will become more apparent as the invention becomes better understood by the detailed description that follows, when considered in connection with the accompanying drawings.

DETAILED DESCRIPTION OF THE PREFERRED EMBODIMENT

This invention relates to a mechanism that enables a person who is unable to breath through the larynx, to produce articulated speech. This invention provides a combination of airflow combined with a sound in a person's mouth that can easily be articulated into speech without having the person use his or her larynx or breathing out of the mouth.

Figure 1:
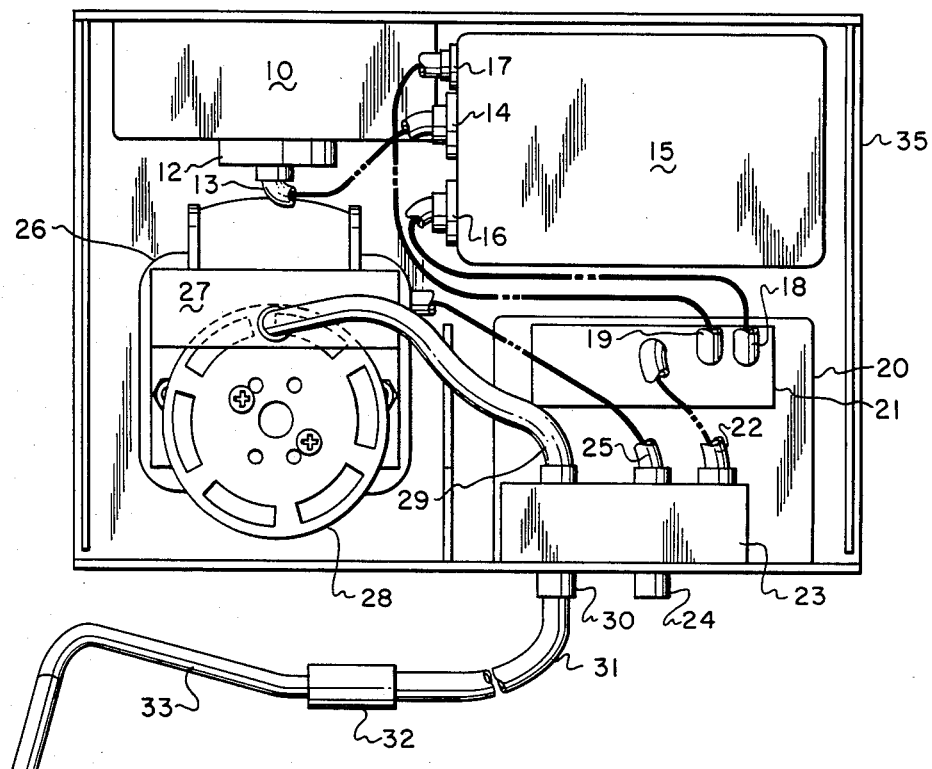
FIG. 1 is a top pictorial view of the invention.

FIG. 1 is a top view of one embodiment of the present invention. The key components illustrated include a filter 10 connected to a pump 15 which is connected to an airflow buffer 20. The buffer 20 is connected to a control mechanism 23 that permits the patient to selectively use the invention. The control mechanism 23 is also connected to a modulation unit or chopper including a motor 26 disk 28 and airflow path mechanism 27 to combine sound with the airflow. The combination of sound and airflow is then transported to a mouthpiece 33.

Specifically the filter 10 is connected to a coupler 12 for receiving atmospheric air outside the container 35. The filter is connected to a coupler 12 which is connected to a tube 13 to permit air input through filter 10 to travel to pump 15 through coupler 14. In this specific embodiment, the pump used is a diaphragm pump which has two outputs through couplers 16 and 17. Tubes 18 and 19 are connected to these couplers 16 and 17 and transport the resulting airflow from pump 15 to the airflow buffer 20 through connecting unit 21. The purpose of the buffer unit 20 is to smooth the airflow between the two outputs to provide a constant airflow since pump 15 is a diaphragm pump providing pulsating airflows through couplers 16 and 17. The output of buffer 20 is connected to tube 22 which is connected to a control mechanism 23 that includes an output coupler 24. Output coupler 24 can be connected through a control tube which is placed in the hand of the user. In this embodiment, when the user blocks the end of the control tube, the airflow is forced back into the control mechanism 23 and out tube 25. If coupler 24 and any connecting tube remains open then the air from pump 15 is pumped back into the atmosphere with very little if any sound. When the air is forced back into tube 25, it is transported to a modulator housing 27. The modulator 27 includes a motor 26 and disk 28 to form what may more descriptively be called a chopper. The airflow from tube 25 flows across the face of disk 28 as this disk 28 rotates within the modulator housing 27. The slots in disk 28 intermittently interrupt the airflow resulting in a sound being combined with the airflow. This combination of sound and airflow is then transported through tube 29 out the control mechanism 23 through connector 30 to a tube 31 that is connected to a mouthpiece 33 with coupler 32. The mouthpiece 33 is placed in the user's mouth and provides the combination of sound and airflow to be articulated by the person into speech.

Figure 2:
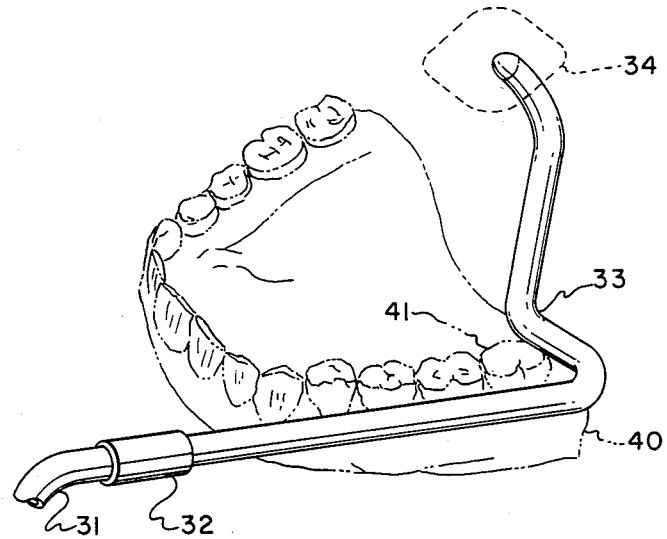
FIG. 2 is a perspective view of the mouthpiece relative in location to a person's set of teeth.

The location of the mouthpiece and the shape of the mouthpiece result in the deposit of the combination of airflow and sound in the person's mouth to provide free movement of the person's lips, jaw and tongue to ease the articulation of the speech. The preferred embodiment of the mouthpiece is illustrated in FIG. 2 which shows the tube 31 connected to a coupler 32 including the mouthpiece 33 located in a person's jaw 40 behind a rearmost molar tooth 41. The opening of mouthpiece 33 shown as area 34 is located in a manner to be above and behind the person's tongue but yet below the roof of the mouth. This position permits the ease of movement of the jaw and tongue to facilitate articulation of the combination of sound and air into speech.

Figure 3:
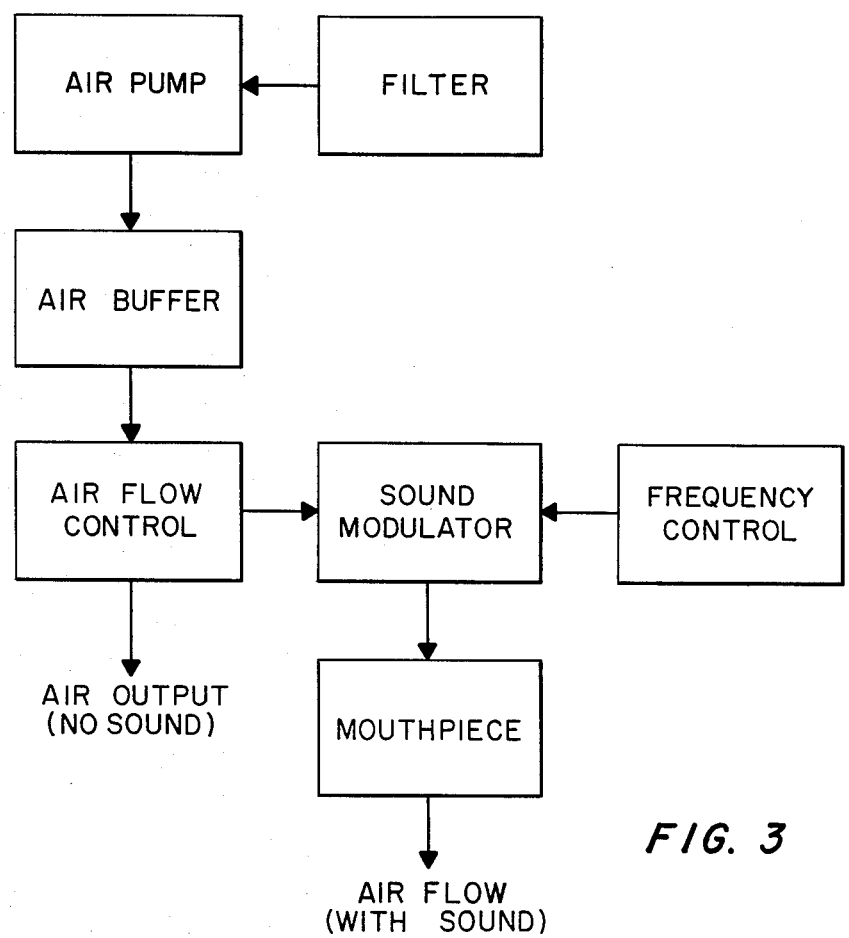
FIG. 3 is a block diagram of the invention.

FIG. 3 illustrates a block diagram for the invention illustrated in FIG. 1. Air input through the filter is transported to an air pump which generates the airflow. In this embodiment, this airflow is transported to an air buffer to smooth the airflow. This smooth airflow is then connected to the airflow control. This airflow control permits the user to selectively direct the air to the sound modulator and then to the mouthpiece in the person's mouth or simply allow the air to go back into the atmosphere and also prevents a continuous tone. This prevents the air from the pump from drying out the user's mouth when the user is not speaking. When the airflow is directed to the sound modulator, the sound modulator produces a sound and combines this sound with the airflow. A frequency control can be used with the sound modulator to provide for a change in frequency of this sound. The combination of sound and frequency is an output to a mouthpiece to be placed inside a person's mouth for articulation and speech.

Figure 4A:
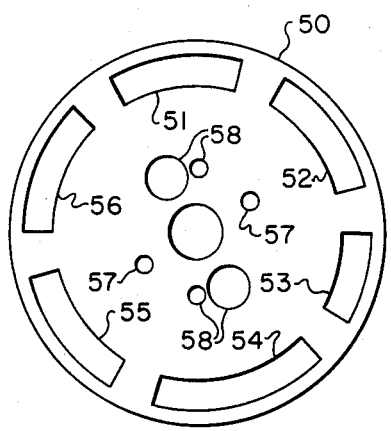
FIG. 4a and 4b are top pictorial views of disks that are used to modulate airflow to produce sound.
Figure 4B:
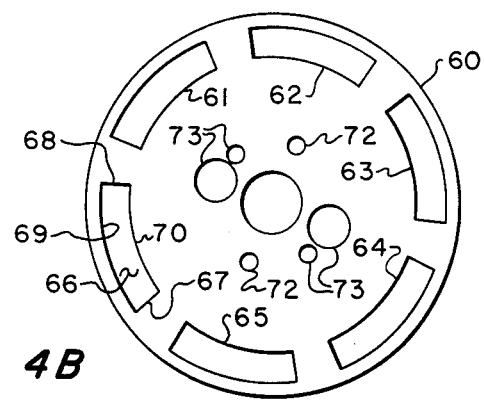
Figure 5:
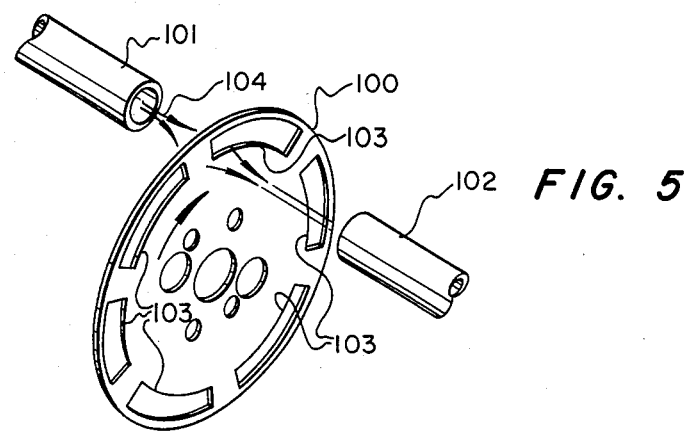
FIG. 5 is a pictorial perspective of the disk relative to the airflow.

The modulator of FIG. 1 can take many forms. The modulator of FIG. 1 includes a disk 28. FIGS. 4a and 4b illustrate two embodiments of this disk. Referring to FIG. 4a, the disk includes holes 58 for mounting on the motor and holes 57 that may by used for placement of screws to secure the disk to the motor mechanism. Slots 51–56 are provided in various shapes. The rotation of thse slots in the path of the airflow (see FIG. 5) intermittently interrupt the airflow and result in the production sound with the airflow. Referring to FIG. 5, airflow 104 from tube 101 is intermittently interrupted by the rotation of the disk 103. This can be seen by the rotation of slots 103 of disk 100. These slots 103 intermittently interrupt the airflow 104 as it attempts to pass to tube 102. In FIG. 4b another embodiment of the disk is shown as disk 60 including slots 61–66. Again holes 73 are provided for mounting the disk on the motor and holes 72 are provided to allow screws to secure the disk 60 to the motor. It should be noted that slots such as 66 may be varied in shape and size such that walls 67, 68, 69 and 70 may be different shapes to produce sound with different overtones. Additionally using this modulation technique with the disk, the location of slots, the pattern of slots, the thickness of the disk and the speed of disk rotation together with the shape of the slots can be varied to produce sounds with various characteristics.

Figure 6:
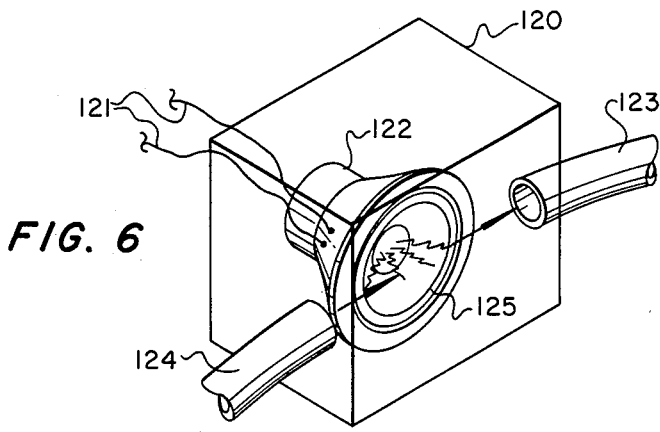
FIG. 6 is a pictorial view of a modulator including a speaker placed within an airflow path.

Another embodiment of the modulator is illustrated in FIG. 6 and includes an enclosure 120 containing a speaker 122 with two wires 121 that can be connected to a signal source. Airflow is placed into enclosure 120 through tube 124 across the face 125 of the speaker 122 and out through tube 123. In this manner the signal generator not shown connected by lines 121 can cause speaker 122 to emit a sound in the presence of the airflow.

Figure 7:
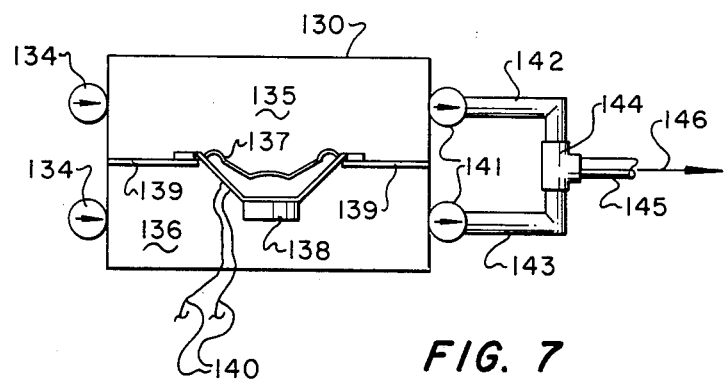
FIG. 7 is a schematic view of an embodiment including a speaker positioned to produce both sound and airflow.

Another embodiment of this invention is illustrated in FIG. 7. FIG. 7 illustrates a schematic representation of an enclosure 130 that serves as both a pump and sounding source to produce the sound combined with an airflow. Enclosure 130 is connected to two input valves 134 to receive air. These input valves 134 provide for a flow of air only into enclosure 130 and not out of enclosure 130. Enclosure 130 further includes a wall 139 with a speaker 138 mounted upon it. The wall 139 and speaker 138 combine to form a first chamber 135 and a second chamber 136 in enclosure 130. The opposite side of enclosure 130 is connected to two output valves 141 which allow only airflow out of the enclosure 130. Valves 141 are connected to tubes 142 and 143. Tubes 142 and 143 are connected to a "T" section 144 which is in turn connected to a tube 145 which provides the combination of sound and airflow 146. Speaker 138 is mounted such that the speaker face 137 is directed towards the first chamber 135. In operation leads 140 connected to speaker 138 are connected to a signal source which produces electrical signals coupled to speaker 138 through wires 140 to cause the speaker face 137 to vibrate. The vibration of faec 137 causes pressure differentials resulting in airflow through input valves 134 and through the output valves 141. The resulting airflow includes sound from the speaker 138. It should be understood that this mehcanism may be used only as a source of airflow, i.e. similar to a diaphragm pump, and placed in combination with a sounding device.

Figure 8:
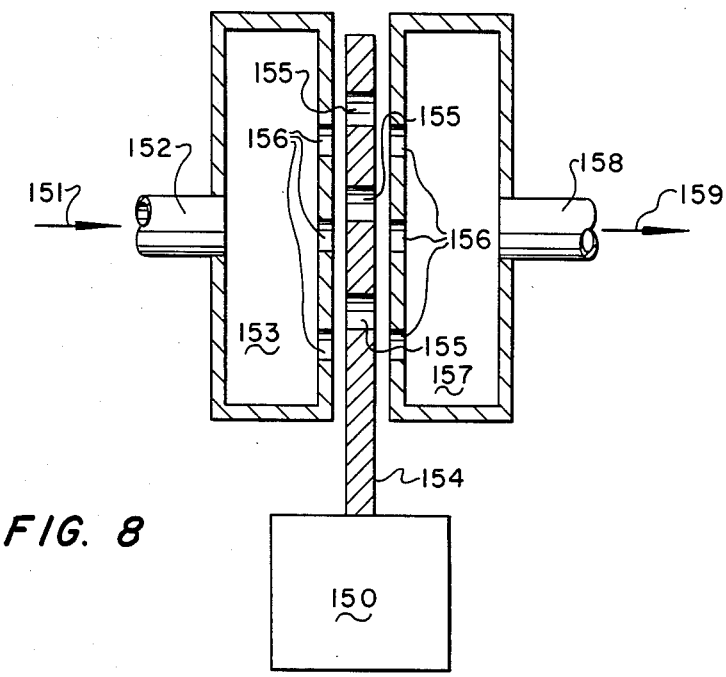
FIG. 8 is a cross-sectional pictorial view of a modulator including a plate mounted on an oscillator.
Figure 9:
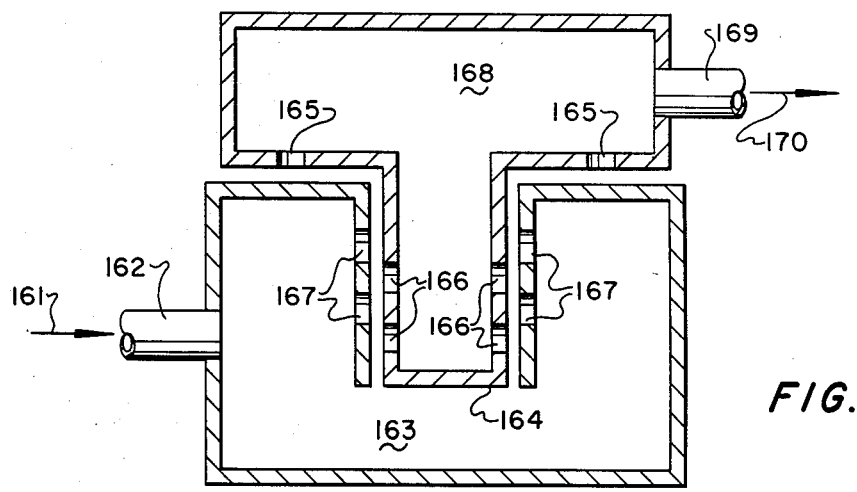
FIG. 9 is a cross-sectional pictorial view of a second embodiment of the modulator of FIG. 8.

FIGS. 8 and 9 illustrate two additional modulator embodiments. In FIG. 8, an airflow 151 enters a first enclosure 153 through tube 152. Plate 154 is connected to an oscillating source 150 such as a solenoid. When plate 154 oscillates up and down, holes 155 will intermittently align with holes 156 to provide an airflow path to a second enclosure 157. This oscillating action will generate compressions and rarefactions of audible sound that are combined with the airflow 159 and provided through tube 158. In FIG. 9, airflow 161 enters enclosure 163 through tube 162. Enclosure 168 is mounted on a flexible coupling 165. Either enclosure 163 or 168 may be connected to an oscillating source and both may be connected to different oscillators of opposite phase. Holes 167 of enclosure 163 intermittently align with holes 166 of enclosure 168 as a cylindrical portion 164 of enclosure 168 oscillates relative to enclosure 163. The airflow 161 will intermittently flow to enclosure 168 and out tube 169. This intermittent airflow will generate compressions and rarefactions of audible sound which will be combined with the airflow 161 and provided as the airflow and sound combination 170.

Figure 10:
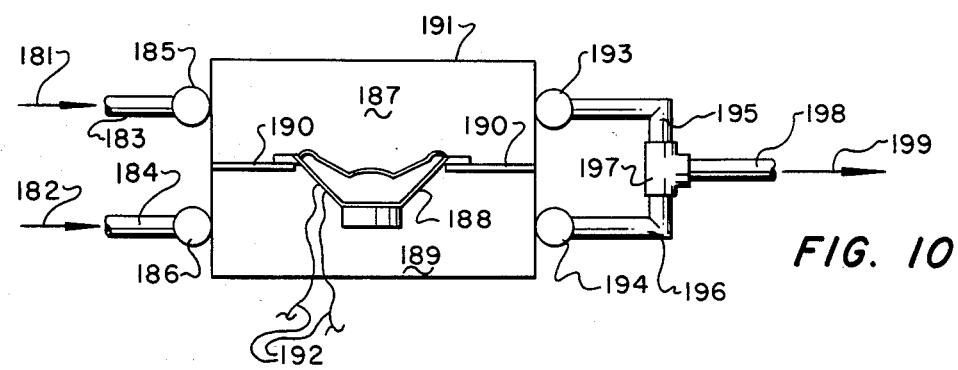
FIG. 10 is a schematic view of a speaker.

FIG. 10 is an embodiment of a speaker apparatus including an enclosure 191 connected to receive two airflows 181 and 182 through tubes 183 and 184 connected to valves 185 and 186. Enclosure 191 includes a wall 190 with a speaker 188 mounted thereupon dividing enclosure 191 into two chambers 187 and 189. Airflow 181 is directed to chamber 187 and airflow 182 is directed to chamber 189. Speaker 188 is connected to a signal source via wires 192 causing the speaker 188 to produce sound which is combined with the airflows in the respective chambers. Valves 193 and 194 are connected to chambers 187 and 189 and provide the output of the combined airflow and sound for each chamber. Tubes 195 and 196 are connected to valves 193 and 194 respectively and also to Tee 197 which combines the two airflows into tube 198 to produce the combination airflow and sound 199.

It should be also understood that the modulator may be located in the mouthpiece. Such a modulator would be a reed that would generate a sound from vibrating in the presence of the airflow. Additionally, the mouthpiece may include a piezo electric transducer connected to an external signal source to generate sound in the mouthpiece in combination with the airflow. The signal source may be controlled by the user to control pitch or volume to vary the resulting speech pattern.

While the preferred embodiments of the invention have been disclosed in detail, various modifications or alterations may be made therein without departing from the spirit or scope of the invention set forth in the appended claims.

What is claimed is:

1. An artificial voice apparatus comprising:
   electronic pump means for producing a continuous airflow within an airflow transmission means from ambient air;
   sounding means connected to said transmission means for combining audible sound with the airflow, including modulation means for modulating the airflow to produce the combination of airflow with the audible sound at a selected frequency;
   mouthpiece means connected to said sounding means for transporting the combined sound and airflow to within a persons mouth wherein said mouthpiece means includes a mouthpiece shaped to permit the person to articulate the combined sound and airflow to produce speech, said mouthpiece depositing the combined airflow and sound by a coupler tube to an area located above and behind the person's tongue but yet below the roof of the mouth, permitting free movement of the person's lips, jaw, and tongue to ease in the articulation of speech.

2. An artificial voice apparatus according to claim 1 wherein said combining means includes an enclosure connected to said transmission means, said enclosure including a speaker, said speaker electrically connected to a signal generation means for producing said sound from said speaker, said enclosure further connected to said mouthpiece means.

3. An artificial voice apparatus according to claim 1 wherein said sounding means include a first enclosure located in proximity to a second enclosure, each enclosure including a plurality of holes upon surfaces of proximity, said holes of said first enclosure in approximate alignment with said holes of said second enclosure, and said sounding means further including a plate including a plurality of holes, said plate mounted upon an oscillating means and extending between said first and second enclosures, said first enclosure connected to receive said airflow and said airflow directed by said first enclosure through said first enclosure holes to said second enclosure holes with said second enclosure connected to said mouthpiece connected to aid mouthpiece means, an said plate oscillating between said enclosures to intermittently interrupt said airflow path.

4. An artificial voice apparatus according to claim 1 wherein said modulation means includes a rotating disk, including a plurality of slots, said disk located in the path of the airflow wherein the rotation of the disk slots intermittently interrupt the airflow.

5. An artificial voice apparatus according to claim 4 wherein the number of slots is selected to produce the selected sound frequency.

6. An artificial voice apparatus according to claim 4 wherein said disk is rotated at a speed to produce the selected sound frequency.

7. An artificial voice apparatus according to claim 4 wherein said slots are of various shapes.

8. An artificial voice apparatus according to claim 4 wherein said slots of said disk are located in preselected positions in said disk 9. An artificial voice apparatus comprising:
   means for producing an airflow within an airflow transmission means for transporting the airflow;
   sounding means connected to said transmission means for combining audible sound with the airflow, said sounding means including a first enclosure located in proximity to a second enclosure, each enclosure including a plurality of holes upon surfaces of proximity, said holes of said first enclosure in approximate alignment with said holes of said second enclosure, and said sounding means further including a plate including a plurality of holes, said plate mounted upon an oscillating means and extending between said first and second enclosure, said first enclosure connected to receive said airflow and said airflow directed by said first enclosure through said first enclosure holes to said second enclosure holes with said second enclosure connected to a mouthpiece means, and said plate oscillating between said enclosures to intermittently interrupt said airflow path; and
   said mouthpiece means connected to said sounding means for transporting the combined sound and airflow to within a person's mouth.

10. An artificial voice apparatus comprising:
    an enclosure including a speaker mounted to divide the enclosure into a first chamber and a second chamber, said speaker having a forward portion facing the first chamber and having a rearward portion facing the second chamber, said first and second chambers connected to a first and second input valve means respectively for providing air into each respective chamber, and said speaker electrically connected to a signal generator for causing the speaker to produce an audible sound and a first and second airflow within said first and second chamber respectively, and
    mouthpiece means connected to said enclosure for transporting the combined sound and airflow to within a person's mouth.

11. A speaker apparatus comprising:
    means for producing a first and second airflow; and
    an enclosure including a speaker mounted to divide the enclosure into a first chamber and a second chamber having a forward portion of the speaker facing said first chamber and having a rearward portion of the speaker facing said second chamber, said first chamber connected to receive said first airflow and said second chamber connected to receive said second airflow, and said speaker electrically connected to a signal source to receive electrical signals for conversion to audible sound which is combined with the airflow in the chambers, asid enclosure further including means for combining and emitting the airflows from said chambers.

12. An artificial voice apparatus comprising:

a pump for producing airflow within a first tube;

control means connected to said first tube for selectively directing the airflow from said first tube to a second tube;

sounding means connected to said second tube for combining said airflow with an audible sound, said sounding means further including a first enclosure located in proximity to a second enclosure, each enclosure including a plurality of holes upon surfaces of proximity, said holes of said first enclosure in approximate alignment with said holes of said second enclosure, and said sounding means further including a plate including a plurality of holes, said plate mounted upon an oscillating means and extending between said first and second enclosures, said first enclosure connected to receive said airflow directed by said first enclosure through said first enclosure holes of said second enclosure holes with said second enclosure connected to a mouthpiece means, and said plate oscillating between said enclosures to intermittently interrupt said airflow path; and said mouthpiece means connected to said sounding means for transporting the combined airflow and sound to a location within a person's mouth.

* * * * *